(12) United States Patent
Wolters et al.

(10) Patent No.: US 9,505,513 B2
(45) Date of Patent: Nov. 29, 2016

(54) DEVICE FOR STERILISING CUBOID-SHAPED CARDBOARD/PLASTIC COMBIPACKS IN AN AUTOCLAVE AND PACK SUITABLE FOR THIS

(75) Inventors: Michael Wolters, Heinsberg (DE); Thomas Dintelmann, Rossdorf (DE)

(73) Assignee: SIG Technology AG, Neuhausen am Rheinfall (CH)

( * ) Notice: Subject to any disclaimer, the term of this patent is extended or adjusted under 35 U.S.C. 154(b) by 780 days.

(21) Appl. No.: 12/675,010

(22) PCT Filed: Sep. 23, 2008

(86) PCT No.: PCT/EP2008/062700
§ 371 (c)(1),
(2), (4) Date: May 26, 2010

(87) PCT Pub. No.: WO2009/040347
PCT Pub. Date: Apr. 2, 2009

(65) Prior Publication Data
US 2011/0111149 A1    May 12, 2011

(30) Foreign Application Priority Data
Sep. 24, 2007  (DE) .......................... 10 2007 045 720

(51) Int. Cl.
*A61L 2/20*        (2006.01)
*B65B 55/06*    (2006.01)
(Continued)

(52) U.S. Cl.
CPC ................ *B65B 55/06* (2013.01); *A23L 3/001* (2013.01); *A23L 3/10* (2013.01); *A23L 3/14* (2013.01); *A61L 2/04* (2013.01); *B32B 27/10* (2013.01); *D21H 17/00* (2013.01); *D21H 19/10* (2013.01); *D21H 21/16* (2013.01); *D21H 27/00* (2013.01); *D21H 27/30* (2013.01); *B32B 2307/412* (2013.01); *B32B 2307/72* (2013.01);
(Continued)

(58) Field of Classification Search
CPC .................................... A61L 2/18; A61L 2/20
USPC ......................................................... 422/292
See application file for complete search history.

(56) References Cited

U.S. PATENT DOCUMENTS

| 4,003,302 A | 1/1977 | Mencacci et al. |
| 5,705,127 A | 1/1998 | Planck, Jr. et al. |

(Continued)

FOREIGN PATENT DOCUMENTS

| DE | 10233095 A1 | 2/2004 |
| EP | 0724887 A1 | 8/1996 |

(Continued)

*Primary Examiner* — Sean E Conley
(74) *Attorney, Agent, or Firm* — The Webb Law Firm

(57) ABSTRACT

A device for sterilizing cuboid-shaped cardboard/plastic combipacks in an autoclave, wherein the packs consisting of product and packing are subjected to heat treatment at a certain temperature over a certain period of time, wherein the product consists of a liquid and chunky portions, and wherein mechanisms are provided inside the autoclave to drive the packs rotationally about a rotational spindle, and a cuboid-shaped cardboard/plastic combipack for use in such a device.

A plurality of packs, are arranged closely adjacent to one another in parallel rows, to be arranged on support floors and for a plurality of support floors loaded with packs to be arranged one above the other and fixed in their mutual positions. The cardboard for the pack used therewith is made water-repellent by means of glue to reduce the intake of water.

11 Claims, 4 Drawing Sheets

(51) Int. Cl.

| | | |
|---|---|---|
| *A23L 3/00* | (2006.01) | |
| *A23L 3/10* | (2006.01) | |
| *A23L 3/14* | (2006.01) | |
| *B32B 27/10* | (2006.01) | |
| *D21H 17/00* | (2006.01) | |
| *D21H 19/10* | (2006.01) | |
| *D21H 21/16* | (2006.01) | |
| *D21H 27/00* | (2006.01) | |
| *D21H 27/30* | (2006.01) | |
| *A61L 2/04* | (2006.01) | |

(52) U.S. Cl.
CPC ........ *B32B2307/73* (2013.01); *B32B 2439/00* (2013.01); *Y10T 428/1303* (2015.01)

(56) References Cited

U.S. PATENT DOCUMENTS

| | | | |
|---|---|---|---|
| 5,849,246 | A | 12/1998 | Hashimoto et al. |
| 6,009,800 | A | 1/2000 | Planck, Jr. et al. |
| 2004/0104246 | A1* | 6/2004 | Kawaguchi et al. ........... 222/83 |
| 2006/0266226 | A1 | 11/2006 | Persoons |
| 2007/0280044 | A1* | 12/2007 | Persoons et al. ............. 366/279 |

FOREIGN PATENT DOCUMENTS

| | | |
|---|---|---|
| EP | 1382353 A1 | 1/2004 |
| EP | 1862082 A2 | 12/2007 |
| FR | 2290249 | 6/1976 |
| GB | 759238 | 10/1956 |
| GB | 762335 | 11/1956 |
| GB | 2040668 A | 9/1980 |
| JP | 9028772 A | 2/1997 |
| JP | 9215733 A | 8/1997 |
| JP | 10033643 A | 2/1998 |
| JP | 10272171 A | 10/1998 |
| JP | 2001231520 A | 8/2001 |
| JP | 2002101862 A | 4/2002 |
| JP | 2003319768 A | 11/2003 |
| WO | 9702181 A1 | 1/1997 |
| WO | 9816431 A1 | 4/1998 |
| WO | 0228721 A1 | 4/2002 |
| WO | 02090206 A1 | 11/2002 |
| WO | 03103417 A1 | 12/2003 |
| WO | 2004014740 A2 | 2/2004 |
| WO | 2008037078 A1 | 4/2008 |

* cited by examiner

DEVICE FOR STERILISING CUBOID-SHAPED CARDBOARD/PLASTIC COMBIPACKS IN AN AUTOCLAVE AND PACK SUITABLE FOR THIS

BACKGROUND OF THE INVENTION

The invention relates to a device for sterilizing cuboid-shaped cardboard/plastic combipacks in an autoclave, wherein the packs consisting of product and packing are subjected to heat treatment at a certain temperature over a certain period of time, wherein the product consists of a liquid and chunky portions, and wherein mechanisms are provided inside the autoclave to drive the packs rotationally about a rotational spindle, and relates to a cuboid-shaped cardboard/plastic combipack for use in such a device.

DESCRIPTION OF RELATED ART

Subjecting products packed in portions to a so-called autoclave process, such as for example foodstuffs for the purpose of preserving them, has been known for a long time. In this connection, tins for example, into which foodstuffs have been previously packed, are exposed to a particular temperature for a specific period of time in an autoclave in order to reliably kill the germs existing in the product and/or the tin. Tins have therefore proved a success for the purpose mentioned particularly because they are not sensitive to the conditions prevailing in an autoclave (high temperature, high humidity, high pressure).

However, if foodstuffs or other products to be sterilised are launched on the market, which are not in tins but are in other forms of packing, the packing—with a relatively high amount of effort and expense—initially has to be sterilised, then the packing has to be filled with the product under sterile conditions and finally the packing has to be aseptically closed. In this way, manufactured cardboard/plastic combipacks are able to store products like, for example, milk or pureed vegetables over a relatively long period of time.

A generic device is known from DE 102 33 095 A1. By means of a rotating autoclave process for sterilizing foodstuffs, cardboard/plastic combipacks are moved during treatment in such a way that the pack contents are constantly mixed thoroughly during the autoclave process. The means used for this purpose are, however, extremely laborious, so that this process cannot be carried out in a commercially acceptable way.

SUMMARY OF THE INVENTION

Using this as a starting point, the object forming the basis of the present invention is to develop and enhance the device mentioned in the introduction and the packs used therein, so that a relatively large number of packs can be satisfactorily sterilised without the packs becoming deformed or their printed design becoming damaged.

With regard to the device having the features of the preamble of claim 1, the solution consists of a plurality of packs, arranged closely adjacent to one another in parallel rows, being arranged on support floors and of a plurality of support floors loaded with packs being arranged one above the other and fixed in their mutual positions.

These "packets" of level pack positions can be fixed in their mutual positions for example by a deadlock by means of generally known pneumatic mechanisms, so that they can rotate in the rotating autoclave without positional changes of individual packs to be treated being required. Advantageously, for this purpose, another support floor is located on the uppermost pack position, which effectively acts as a "lid". The individual support floors can, moreover, be fixed in position stably by generally known centring attachments at the desired parallel distance apart from one another.

Alternatively, an essentially cuboid-shaped frame assembly can be provided to accommodate the pack, which contains a plurality of tray-like insert plates, arranged one above the other, to accommodate a plurality of packs arranged closely behind one another in parallel rows and lying on their narrow sides.

The invention has recognised that damage to the printed design or even deformation of the pack can be reliably eliminated as a result of the packs to be sterilised being fixed or guided inside the autoclave, by means of the specially designed support floors and insert plates, such that when rotating, on the one hand, the contents of the pack are simultaneously thoroughly mixed and, on the other hand, sufficient contact is guaranteed between hot steam or hot plate sections and the pack surface.

Sterilising packs made of commercially available packing materials satisfactorily, causes dents, bruises and/or bubbles, as well as damage to the printed design on the pack, due to local drenching of the cardboard. Due to the high temperatures, high humidity and high pressure in the autoclave, the commercially available composite structure is weakened such that undesired indentations by the pack fixing elements occur. Packing material delaminations can also in part occur. Furthermore, further damage can occur when removing the softened packs.

The rotation process, for reasons inherent in the system, suffers from the higher demands of the seams and cut edges of the pack, so that, irrespective of the rotational direction and arrangement of the packs in the autoclave, the partly liquid and partly gaseous heating and cooling agents occasionally impinging, contrary to the static process, cannot be prevented. Therefore, conventional packs cannot withstand these increased demands.

With regard to the packs used, this problem is solved by the cardboard being made water-repellent by means of glue to reduce the intake of water and by the amount of glue used being between 1 and 4 kg/t of dry pulp.

According to another teaching of the invention, in the design with a frame assembly, provision is made for the autoclave to be a steam/air rotating autoclave or a sprinkling rotating autoclave. Due to the modular and compact construction of the device according to the invention, commercially available rotating autoclaves can be easily used.

According to another embodiment of the invention, the frame assembly has at least one hinged lid. This is particularly advantageous, as a lid only needs to be locked in order to fix the insert plates in place after loading so that they do not lose their mutual positions during rotation. For opening and unloading, the locking device only has to be released in order to be able to open the lid and take out the individual insert plates. Screwing the insert plates securely in position can, therefore, be completely dispensed with.

According to another embodiment of the invention, the frame assembly is provided with wheels, runners, chains or rails or the like to insert things into and take things out of the autoclave more easily, which wheels, runners, chains or rails or the like can be driven on corresponding, horizontal rails, guides or rollers in order to facilitate the autoclave loading process.

Another teaching of the invention makes provision for each insert plate to have a circumferential frame and dividing plates running between the pack rows. In this way, the packs are fixed in position over a large area and are spared damage by deformation. Preferably, the frame and/or the dividing plates are designed to be hollow, and have recesses to enable the sterilizing medium to circulate well inside the autoclave. The recesses in another embodiment of the invention are arranged so that the packs on the touching contact surfaces do not lie in the area of recesses. The packs can hereby also be spared damage by deformation in the most advantageous way.

The invention has, in addition, recognised that it is advantageous if the floor of each insert plate has no recesses or holes. Furthermore, the floor of each insert plate can be designed as a hollow floor, so that air or steam can flow through it for better temperature control.

In another embodiment of the invention, the insert plates are designed so that at loading temperature a narrow air gap exists between the floor of an insert plate and the surfaces of the packs located underneath. The width of the air gap is—at loading temperature—0.5 to 10 mm, preferably 3 to 5 mm. The counter pressure in the rotating autoclave is driven at a temperature of above 100° C. such that the packing is jammed or fixed between the parallel faces of the autoclave trays by means of thermal expansion of the packing in conjunction with the expansion of the ullage and the expansion of the gas bubble, and in such a way damage to the packing is avoided.

It has also been demonstrated that a good sterilisation result can be obtained if the longitudinal axis of the pack rows is parallel to the rotational spindle of the autoclave. A technically extremely involved and extensive rotation of the packs to be sterilised about a spatial spindle that is not arranged parallel to the pack edges, as in the generic prior art, can consequently be dispensed with.

Another teaching of the invention makes provision for the density of the raw cardboard used to be in the range of 680 to 860 kg/m$^3$. Preferably, the freeness value of the cardboard fibres used for the pack is 15 to 35 SR. Such a material can withstand the extreme conditions prevailing in the autoclave well.

According to another development of the invention, the surfaces of the packs are imprinted so as to be water-repellent and/or the imprint is protected by a transparent plastic coating. Damage to the printed design through abrasion and blistering or discolouring is reliably eliminated by this embodiment.

Particularly good sterilisation can then be obtained if the filling quantity of the packs used is chosen so that a gas bubble of 2 to 30% of the nominal volume of the pack exists inside them. By that means and the chunky portions found in the product, the contents of the pack are thoroughly mixed uniformly and constantly during rotation in the autoclave. This leads to considerably shorter treatment times, resulting in further protection of the packs used. Nitrogen, for example, can be used as the gas in the manner known.

Another development of the invention makes provision for the cut edges of the packs to be additionally pressed. Whilst the pack surfaces are relatively well protected against ingress of moisture by the PP coating and/or the water-repellent imprinting, the "open" cut edges are at risk in the area of the seams. For this reason, an additional pressing operation prevents the ingress of steam or moisture into the composite material.

According to another teaching of the invention, scavengers can be used to absorb the proportion of oxygen in the cardboard/plastic composite material. The use of such "oxygen interceptors" in packing material is already known per se.

BRIEF DESCRIPTION OF THE DRAWINGS

The invention will be explained in more detail below by means of a drawing depicting only one exemplary embodiment. In the drawing.

DETAILED DESCRIPTION OF THE INVENTION

Figure 1:
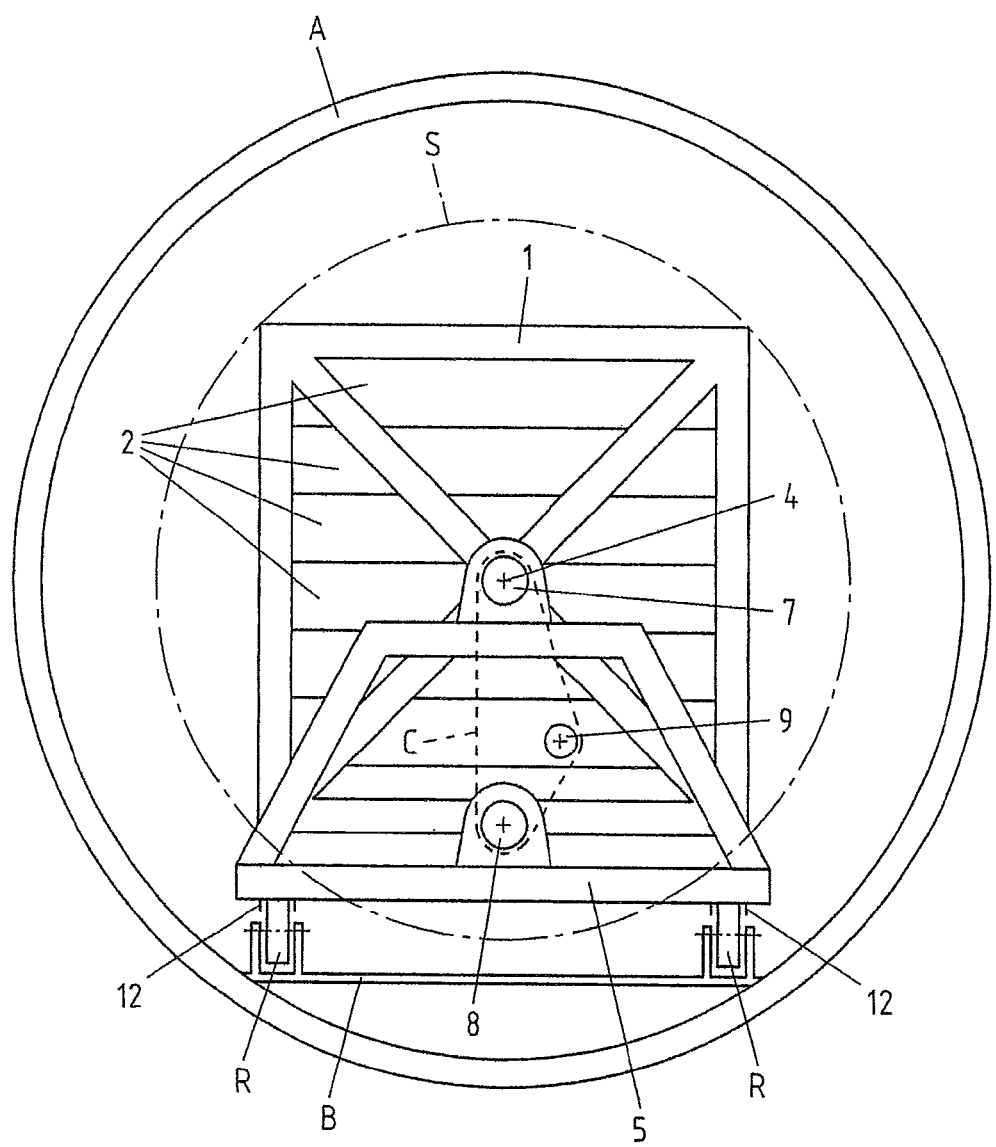
FIG. 1 shows a frontal view of an exemplary embodiment of the device according to the invention in an autoclave only indicated schematically.
Figure 2:
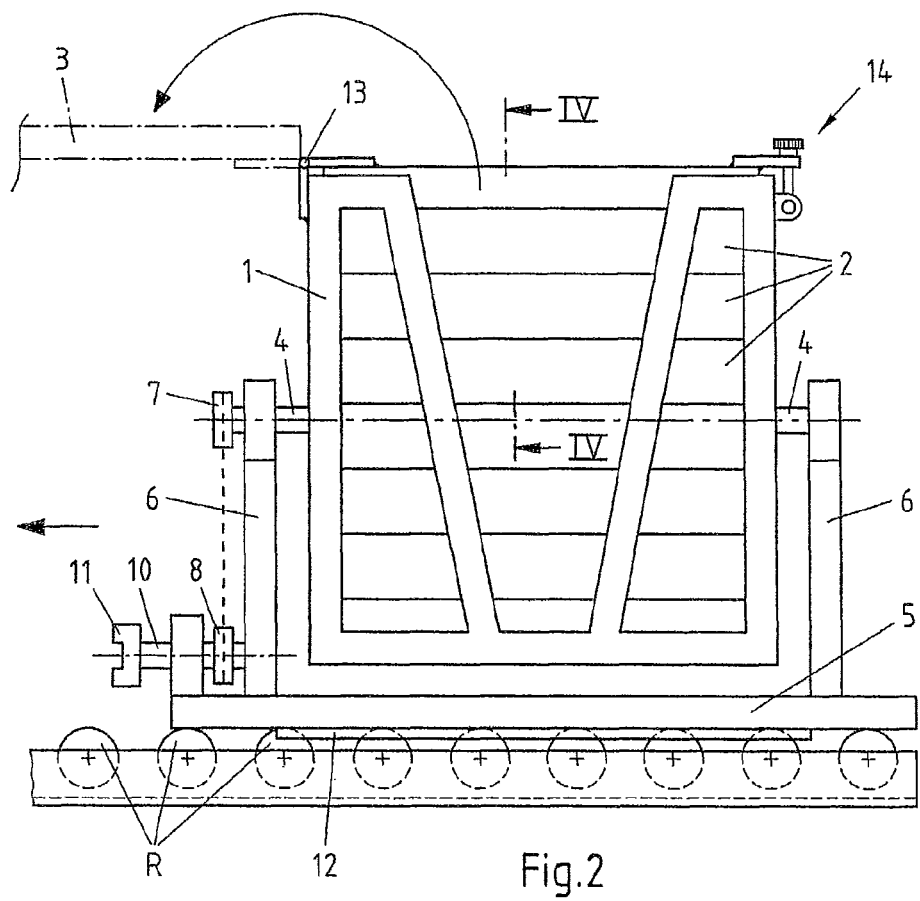
FIG. 2 shows a side view of the device according to the invention from FIG. 1.
Figure 3:
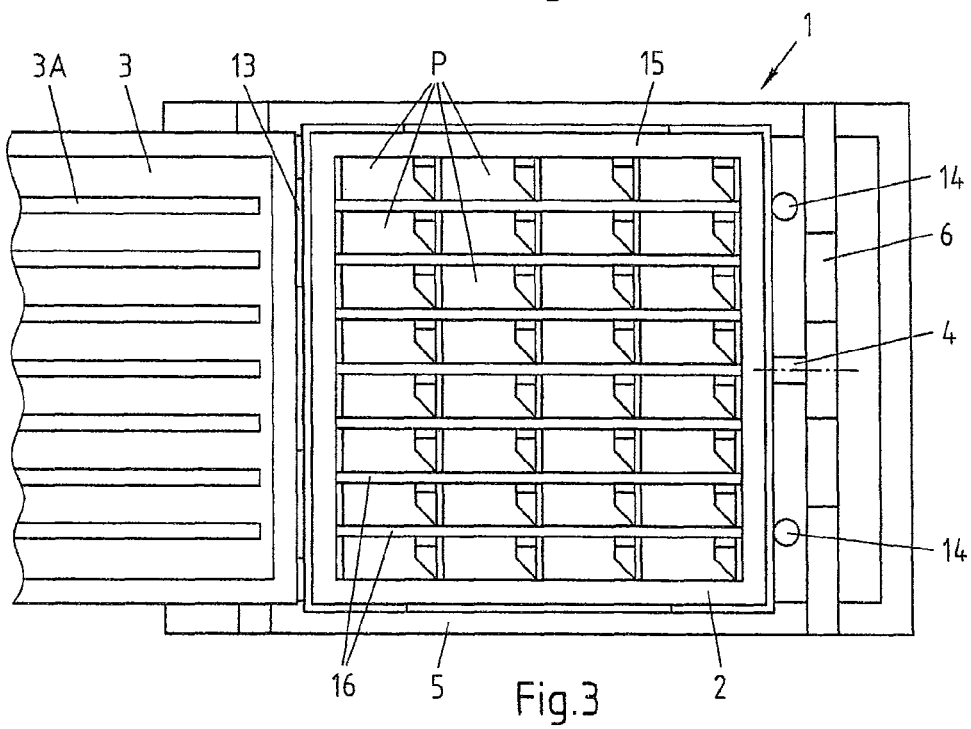
FIG. 3 shows a plan view of the device according to the invention from FIG. 1, but with the lid open.

The device according to the invention for sterilizing cuboid-shaped cardboard/plastic combipacks firstly consists, as can be seen from FIGS. 1 to 3, of a frame assembly 1, in which a plurality of insert plates 2 are inserted. The frame assembly 1 has a lockable lid 3 so that during rotation of the frame assembly 1 the insert plates 2 do not fall out of it.

As already mentioned, the invention also, however, comprises "frameless" configurations, in which the packs, arranged above one another in a plurality of levels, for the purpose of fixing are jammed against one another, but here, by way of example, a device having a frame assembly 1 shall be explained.

The frame assembly 1 is rotatably mounted via spindles 4 in lateral supports 6 located on a base frame 5. In order to apply the necessary torque, the rotational spindle 4, arranged on the left in FIG. 2, is provided on the end with a chain wheel 7 which via a chain C, illustrated with a dashed line, is connected to another chain wheel 8 and a tensioning wheel 9, indicated only in FIG. 1, having a drive shaft 10 which on the end has a claw coupling 11 which when entering the autoclave A in the direction of the arrow, which is not indicated in more detail, operatively connects to a corresponding coupling of a drive motor (not illustrated).

To make the loading process easier, the base frame 5 has guide rails 12 on its underside, which serve for guiding along rollers R attached in a freely rotating manner to a base B of the autoclave A, as clearly emerges from FIGS. 1 and 2.

It can also be gathered from FIG. 2 that the lid 3 is attached to the frame assembly 1 by means of a hinge 13 and can be locked in its closed position by means of two locking devices 14. The closed frame assembly 1 can then be rotated inside the autoclave A about the rotational spindle 4; the associated pivot circle S is illustrated as a dot-dashed line in FIG. 1.

It now emerges from FIG. 3 that each insert plate 2, only the uppermost of which can be seen with the lid 3 open, has a circumferential frame 15 which forms the lateral boundary of a plurality of packs P. So that the packs P can be arranged in uniform longitudinal rows one behind the other and lying on their narrow sides within the insert plate 2, each insert plate 2 has dividing plates 16 running the entire length of the insert plate 2, which form a lateral boundary for the adjacent pack rows.

Figure 4:
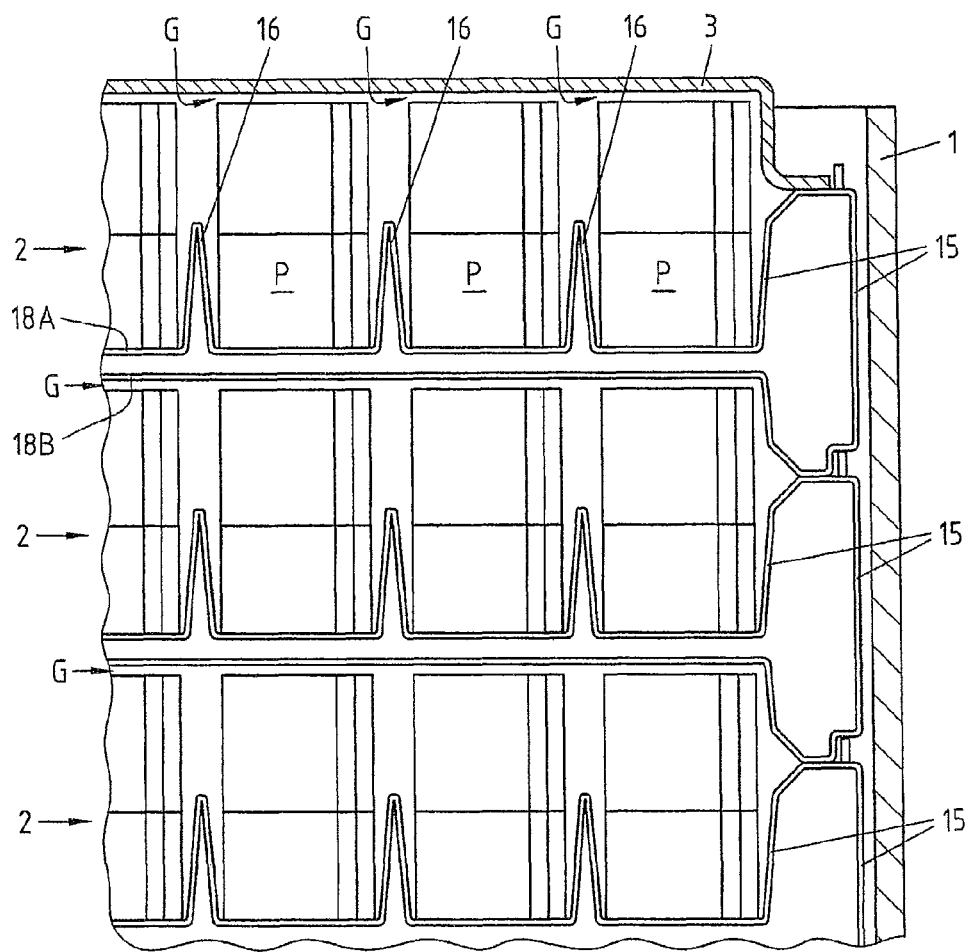
FIG. 4 shows an enlarged cross-section through the upper part of the device according to the invention, in the direction of the arrows IV-IV in FIG. 2.

The exact configuration of the insert plates 2 according to the invention can be taken from FIG. 4, in which the upper part of a packet of insert plates 2 from FIG. 2 is shown in cross-section in the direction of the arrows IV-IV. Here, it must firstly be seen that the frame 15 of the insert plates 2 is designed to be hollow and extends so far down that it effectively at the same time forms an upper "lid" for the packs P arranged under it. The lid 3 hence has the same form on its underside. It can also be seen that the dividing plates 16 are arranged so that they taper upwards, but in each case define a pack width at the bottom. Such a configuration enables the packs P to move sideways easily during the rotation process in the autoclave A.

Figure 5:
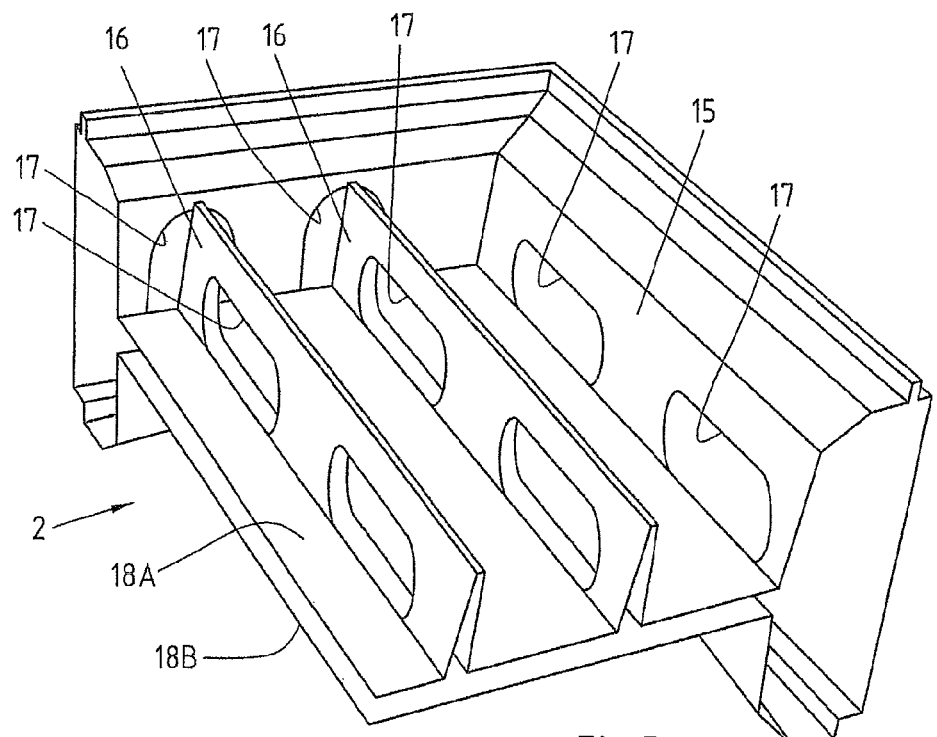
FIG. 5 shows a corner section of an empty insert plate illustrated in perspective view and FIG. 6 shows the corner section from FIG. 5 with a pack inserted.
Figure 6:
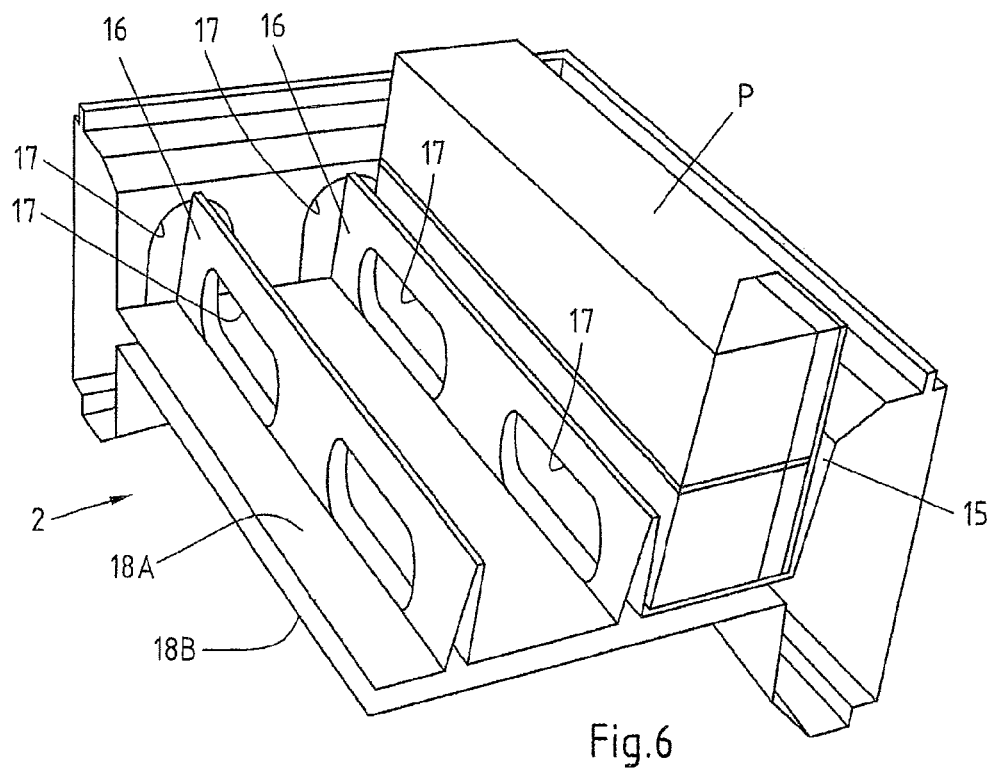

So that the sterilizing medium can also now be distributed most favourably in the region of the insert plates 2, both the frame 15 and the dividing plates 16 have recesses 17. The floor 18 of the insert plates 2 is designed as a hollow floor, i.e., here it consists of an upper floor 18A and a lower floor 18B, as is clearly shown in the perspective illustrations according to FIG. 5 and FIG. 6. This design has the advantage that the closed floors 18A, which are not provided with recesses or holes, provide optimum support to the narrow longitudinal sides of the packs P. To provide a better overview, a pack P inserted into the insert plate 2 shown is illustrated. Owing to the fact that above the insert plate 2 shown another insert plate 2 or the lid 3 (which lid 3 is also provided with slits 3A) restricts pack rows in the upward direction, the frame assembly 1 is correspondingly supported during rotation. The slits 3A are arranged for this purpose, as emerges from FIG. 3, exactly above the dividing plates 16.

The height of the insert plates 2 is thereby selected so that at loading temperature a narrow air gap G exists between the floor 18B of an insert plate 2 and the surfaces of the packs P located underneath, as emerges from FIG. 4. Preferably, the width of the gap (G) at loading temperature is 0.5 to 10 mm.

The invention claimed is:

1. A device for sterilizing cuboid-shaped cardboard/plastic combipacks in an autoclave, wherein packs consisting of product and packing are subjected to heat treatment at a certain temperature over a certain period of time, wherein the product consists of a liquid and chunky portions, and wherein mechanisms are provided inside the autoclave to drive the packs rotationally about a rotational spindle, wherein a plurality of packs, arranged closely adjacent to one another in parallel rows, are arranged on support floors, and wherein a plurality of support floors loaded with packs are arranged one above the other and fixed in their mutual positions, the device comprising:

an essentially cuboid-shaped integral frame assembly provided to accommodate the packs, the frame assembly including a plurality of tray insert plates, arranged one above the other, to accommodate a plurality of the packs arranged closely behind one another in parallel rows and lying on their narrow sides, wherein the insert plates are designed so that at loading temperature a narrow air gap exists between a floor of each insert plate and the surfaces of the packs, located underneath, of the insert plate arranged underneath, and wherein the entire floor of each insert plate has no recesses or holes, wherein an entire bottom surface of each pack rests on the corresponding floor of each insert plate, wherein each insert plate has dividing plates running between the sides of the packs, and wherein the dividing plates are hollow with recesses extending through the dividing plates.

2. The device according to claim 1, wherein the autoclave is a steam/air rotating autoclave.

3. The device according to claim 1, wherein the autoclave is a sprinkling rotating autoclave.

4. The device according to claim 1, wherein the frame assembly has at least one hinged lid.

5. The device according to claim 1, wherein the frame assembly has wheels, runners, chains and/or rails to insert things into and take things out of the autoclave more easily.

6. The device according to claim 1, wherein each insert plate has a circumferential frame and dividing plates running between the sides of the packs.

7. The device according to claim 6, wherein the circumferential frame and the dividing plates are designed to be hollow, and have recesses.

8. The device according to claim 7, wherein the recesses are arranged so that the packs on touching contact surfaces do not lie in the area of recesses.

9. The device according to claim 1, wherein the floor of each insert plate is designed as a hollow floor, so that air or steam can flow between an upper and a lower plate.

10. The device according to claim 1, wherein the width of the air gap is 0.5 to 10 mm.

11. The device according to claim 10, wherein the width of the air gap at loading temperature is 3 to 5 mm.

\* \* \* \* \*